United States Patent [19]
Huth et al.

[11] Patent Number: 5,351,029
[45] Date of Patent: Sep. 27, 1994

[54] SENSOR FOR DETERMINING CARBON MONOXIDE

[75] Inventors: Gerhard Huth, Gerlingen; Detlef Baresel, Stuttgart, both of Fed. Rep. of Germany

[73] Assignee: Robert Bosch GmbH, Stuttgart, Fed. Rep. of Germany

[21] Appl. No.: 78,291
[22] PCT Filed: Dec. 18, 1991
[86] PCT No.: PCT/DE91/00986
§ 371 Date: Jun. 22, 1993
§ 102(e) Date: Jun. 22, 1993
[87] PCT Pub. No.: WO92/13270
PCT Pub. Date: Aug. 6, 1992

[30] Foreign Application Priority Data
Jan. 15, 1991 [DE] Fed. Rep. of Germany ....... 4100915

[51] Int. Cl.$^5$ .............................................. H01C 7/00
[52] U.S. Cl. ........................................ 338/34; 422/90
[58] Field of Search ...................... 338/34, 35; 422/90

[56] References Cited

U.S. PATENT DOCUMENTS

| | | | |
|---|---|---|---|
| 4,194,994 | 3/1980 | Baresel et al. | 252/518 |
| 4,579,751 | 4/1986 | Forster | 338/34 X |
| 4,592,967 | 6/1986 | Komatsu et al. | 338/34 X |
| 4,732,738 | 3/1988 | Nakatani et al. | 338/34 X |

FOREIGN PATENT DOCUMENTS

| | | |
|---|---|---|
| 0102067A3 | 3/1984 | European Pat. Off. . |
| 0141033A3 | 5/1985 | European Pat. Off. . |
| 2603785C2 | 8/1984 | Fed. Rep. of Germany . |
| 2648373C2 | 1/1986 | Fed. Rep. of Germany . |
| 3024449C2 | 1/1988 | Fed. Rep. of Germany . |

OTHER PUBLICATIONS

Sensors and Actuators, vol. 6, pp. 35-50 (1984) Barasel et al.

Primary Examiner—Marvin M. Lateef
Attorney, Agent, or Firm—Spencer, Frank & Schneider

[57] ABSTRACT

The invention relates to a sensor for the determination of carbon monoxide, especially in gas mixtures containing oxygen, on the basis of doped metal oxides whose electric conductivity is a function of the composition of the gas mixtures. Suitable metal oxides are those having n-type conductivity, the dopants used being other oxides of a metal having a maximum valency <4; oxides of a metal catalyzing the reaction of carbon monoxide with oxygen to give carbon dioxide, each in amounts from 0.01 to 0.2 mol %; and from 0.001 to 0.1 mol % of an oxide of a metal of the 5th subgroup of the Periodic Table of Elements. The sensors are notable for a small resistance-temperature coefficient while having high sensitivity and low hysteresis.

5 Claims, 2 Drawing Sheets

SENSOR FOR DETERMINING CARBON MONOXIDE

The invention relates to a sensor for the determination of carbon monoxide, especially in gas mixtures containing oxygen, on the basis of doped metal oxides whose electric conductivity or whose electrical resistance is a function of the composition of the gas mixtures.

BACKGROUND OF THE INVENTION

Sensors for carbon monoxide are required, for example for monitoring heating installations on the basis of fossil fuels or of internal combustion engines. In both cases, the objective is, both for economical and ecological reasons, to burn the fossil fuels or the engine fuel as completely as possible. The combustion air is therefore used in a certain excess, so that the exhaust gas still contains oxygen but nevertheless in addition contains small amounts of carbon monoxide. In order to optimize the combustion processes it is useful to know the content of carbon monoxide in the exhaust gas.

Sensors for determining the carbon monoxide content in exhaust gases on the basis of metal oxides whose electric conductivity changes at the prevailing high temperatures as a function of the carbon monoxide content but also of the oxygen content, are known. Thus, the German Patent 26 03 785 describes sensors made of chromium(III) oxide or tin(IV) oxide, which are doped with at least one oxide of the transition metals of the 4th to 6th group of the Periodic Table of the Elements PTE or an oxide of iron, nickel, cobalt, tin, magnesium, calcium or lithium.

The German Patent 26 48 373 discloses sensors comprising semiconductors, which consist of doped tin (IV) oxide, the catalytic activity of the semiconductor for the reaction between oxygen and oxidizable components such as carbon monoxide being specifically reduced. Sensors on the basis of cerium(IV) oxide which is doped with magnesium oxide, aluminum oxide, yttrium oxide, titanium(IV) oxide, tantalum(V) oxide, niobium(V) oxide or vanadium(V) oxide are disclosed in the German Patent 30 24 449.

Finally, in "Sensors and Actuators", 6 (1984), 35–50, there is an article on the influence of the catalytic activity of semiconducting metal oxides on their properties as sensors for carbon monoxide, together with an exhaustive overview of the relevant literature.

Sensors of the type described have become established in practice and on the whole have useful. However, they leave something to be desired where it is a matter determining small amounts of carbon monoxide in gas mixtures whose temperatures fluctuate. In that case, the sensors must combine a high sensitivity with a Low resistance-temperature coefficient. In other words, on the one hand even small fluctuations in the carbon monoxide content should result in distinct changes in the conductivity or the resistance, and on the other hand, the conductivity or the resistance should be, as far as possible, largely independent of the measuring temperature. Furthermore, the prior art sensors are not satisfactory in terms of their useful life. It would therefore be desirable to develop sensors having longer service lives.

SUMMARY OF THE INVENTION

The sensors according to the invention, as described in the claims, have a high sensitivity, especially at low carbon monoxide contents. At the same time, their conductivity varies only slightly as a function of the oxygen content. The measured conductivity is there ore largely determined by the carbon monoxide content. Over wide concentration or partial pressure ranges there is an approximately linear relationship between these two variables. For a given composition of the gas mixture, the sensors according to the invention exhibit, in the industrially significant temperature range from approximately 300° to 700° C., a lower temperature dependence of the conductivity than the known sensors. This applies particularly if they are additionally doped with tantalum(V) oxide. They therefore provide, even without the elaborate compensation circuits required for prior art sensors in the case of large temperature fluctuations in the exhaust gases, good and easily reproducible measuring results. A further advantage of the sensors according to the invention is their extended service life. Useful lives of 5000 hours of service and more can be achieved.

DESCRIPTION OF THE PREFERRED EMBODIMENT

Figure 1:
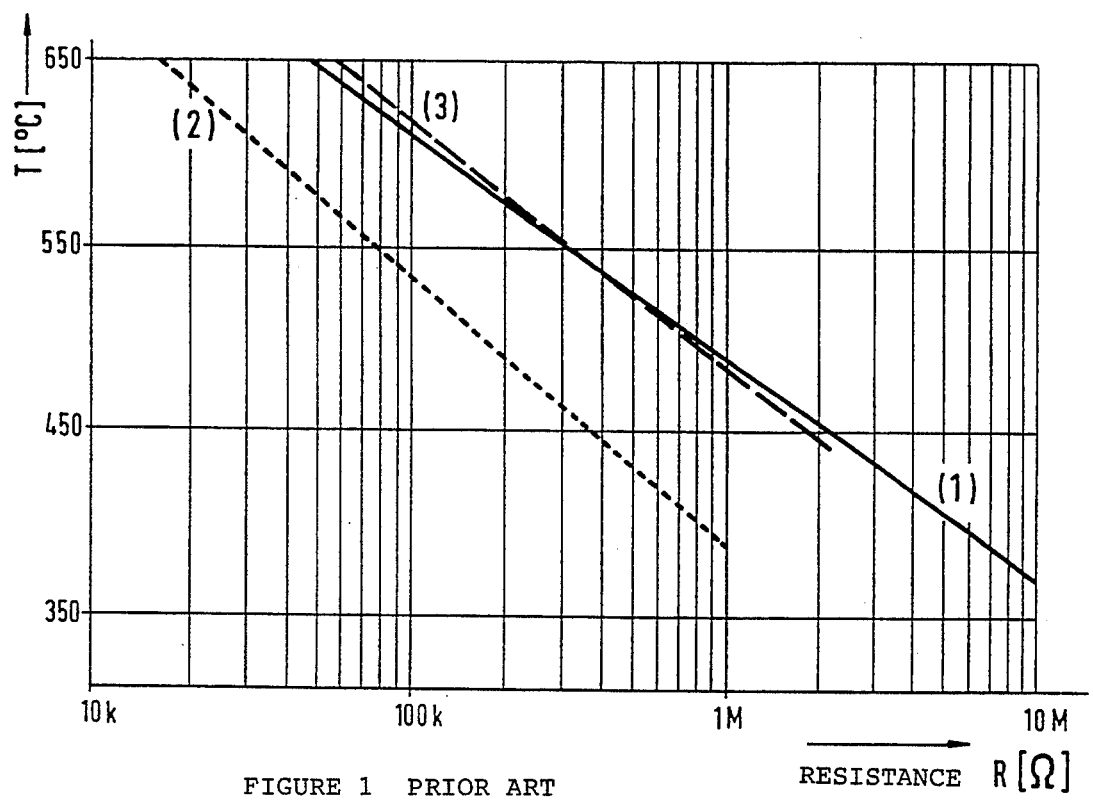
FIG. 1 is a graphic representation depicting resistance - temperature characteristics of a prior art sensor as a logarithmic plot.

The sensors according to the invention are particularly suitable for determining carbon monoxide in lean exhaust gases, i.e. those containing little carbon monoxide and comparatively large amounts of oxygen. The carbon monoxide contents may be, for example, from 5 to 1500 ppm, preferably from 10 to 1200 ppm, the oxygen contents from 2 to 20% by volume, preferably from 2 to 10% by volume. The predominant proportions are nitrogen and carbon dioxide, but the mixture may also contain relatively small amounts of nitrogen oxides and/or unburnt hydrocarbons.

The constituents of the sensors have all been described per se in connection with doped semiconductors. The surprising properties of the sensors according to the invention result from the qualitative and the quantitative selection. Metal oxides having n-type conductivity, as is well known, are those having a slight oxygen deficit with respect to the stoichiometry. Relevant examples are zinc oxide and cerium(IV) oxide. It was found that the suitable materials include tin(IV) oxide.

Examples to be mentioned of oxides of other metals having a maximum valency <4 are aluminum oxide, copper(II) oxide, iron(II) oxide, iron(III) oxide, nickel oxide, cobalt oxide, calcium oxide and strontium oxide. Magnesium oxide is preferred. The metal oxides are added in only small amounts, especially in amounts from 0.05 to 0.15 mol %.

It is important for the function of the sensors that the oxidation of the carbon monoxide to carbon dioxide is indeed catalyzed, but only at a low rate and that it proceeds in any case more slowly than the adsorption of the carbon monoxide onto the oxygen-laden surface of the n-type metal oxide. Accordingly, the catalyst is selected in terms of type and quantity. Examples oxides of metals which catalyze the reaction of carbon monoxide with oxygen to carbon dioxide and which are therefore suitable for sensors according to the invention, are those of the platinum metals platinum, rhodium and ruthenium and especially palladium; the oxides of manganese, chromium, cobalt and nickel can also be used. These constituents are likewise added in only small amounts, in particular in amounts from 0.05 to 0.15 mol %. It is true of both dopants that their optimum proportion - within the wider limits i.e., 0.01 to 0.2 mol % and the narrower limits listed above - depends on the choice of the substances in question and that it can readily be determined by preliminary tests.

A particularly small resistance-temperature coefficient is shown by those sensors in which the n-type metal oxide additionally comprises an oxide of a metal of the 5th subgroup of the Periodic Table of the Elements. viz. of vanadium, niobium and especially tantalum. This additive is likewise used in only small amounts, preferably from 0.003 to 0.03 mol %.

If the two dopants (1) an oxide of another metal having a maximum valency <4, and (2) an oxide of a metal which catalyses the reaction of carbon monoxide to carbon dioxide, and the additive which is an oxide of a metal of the fifth subgroup of the Periodic Table of the Elements are designated as oxides, this is merely to indicate the degree of oxidation of the metal when the sensor is manufactured. In the finished sensors, the metals in question may well exist at least partially in the form of other chemical compounds, for example as stannates, or in metallic form, for example as palladium.

The doped n-type metal oxides are prepared in a conventional manner. Thus, the corresponding metal salts can be dissolved in water in appropriate amounts, and the mixture of the oxides, hydroxides, oxide hydrates and/or carbonates can be precipitated from the solution by means of alkaline substances such as aqueous sodium hydroxide, sodium carbonate solution or aqueous ammonia. The mixture can then be thickened, evaporated to dryness and the water-soluble substances can be leached from the solid phase. Alternatively, the water-soluble components can be isolated, prior to evaporation, by washing and decanting.

The dry doped n-type metal oxide, having been annealed at from 500° to 650° C. if required, is then expediently finely ground, made into a paste and applied to a substrate provided with electrodes, for example made of platinum. The coated substrate is allowed to dry, and the doped n-type metal oxide is activated by gradually heating it on the substrate to a temperature from approximately 800° to 1000° C. and letting it cool down again similarly gradually. The sensor thus obtained can be directly connected into the measuring circuit as a resistor.

EXAMPLE 52 g of tin(IV) chloride, 40.6 mg of magnesium chloride hexahydrate, 10.6 mg of palladium chloride and 7.6 mg of tantalum(V) chloride are dissolved in 2 l of water, and the solution is heated to 80° C. While the solution is stirred vigorously, an aqueous 10% strength ammonia solution is added at a rate of 1 drop per second until a pH of 8 is achieved. The temperature is raised to 90° C., and the batch is held at this temperature for 3 hours, the mixture becoming viscous. The whole batch is evaporated to dryness in air within 10 hours at a bath temperature of 130° C. After cooling, the solid mass is slurried with 3 l of water, is digested for 4 hours and the water is decanted. This treatment is repeated with 4 l of water. The coarsely crystalline composition is heated in a tube furnace, with a temperature increase of 50° C./h, to 600° C. and kept at this temperature for 5 hours. The composition is allowed to cool down to room temperature, with a cooling rate of 100° C./h, is mixed with toluene (15 g per 10 g of dry composition) and the mixture is ground for 24 hours in a high-speed hard-metal ball mill. The ground material is dried for 4 hours in air, and the remaining toluene is removed in a vacuum drying oven at 100° C. and approximately 0.01 torr.

To prepare the paste to be blade-coated onto the aluminum oxide substrate, the dry powder is mixed with a "bodied oil" (50% of benzyl alcohol, 30% of ethyl cellulose, 20% of terpineol); the volume ratio powder:paste is approximately 1:1. To fabricate the sensor, the paste is applied onto a ceramic substrate, which on its topside is provided with two platinum electrodes and on its underside is provided with a printed platinum heating meander, in such a way that the layer having a thickness of approximately 0.1 mm appears to be uniform. The coated substrate is left to lie in air at 70° C. for approximately 10 minutes and is then heated gradually (temperature increase approximately 20° C./h) to 900° C. After this temperature has been maintained for 2 hours, the sensor is allowed to cool to room temperature, employing a temperature reduction of approximately 100° C./h.

Figure 2:
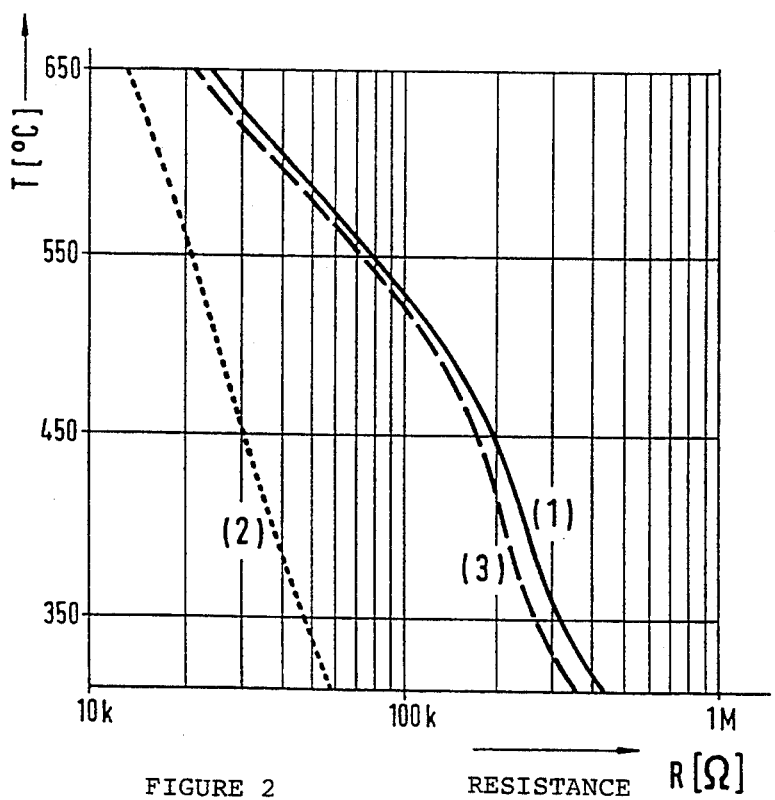
FIG. 2 is a graphic representation depicting resistance - temperature characteristics of a carbon monoxide sensor of the present invention as a logarithmic plot.
Figure 3:
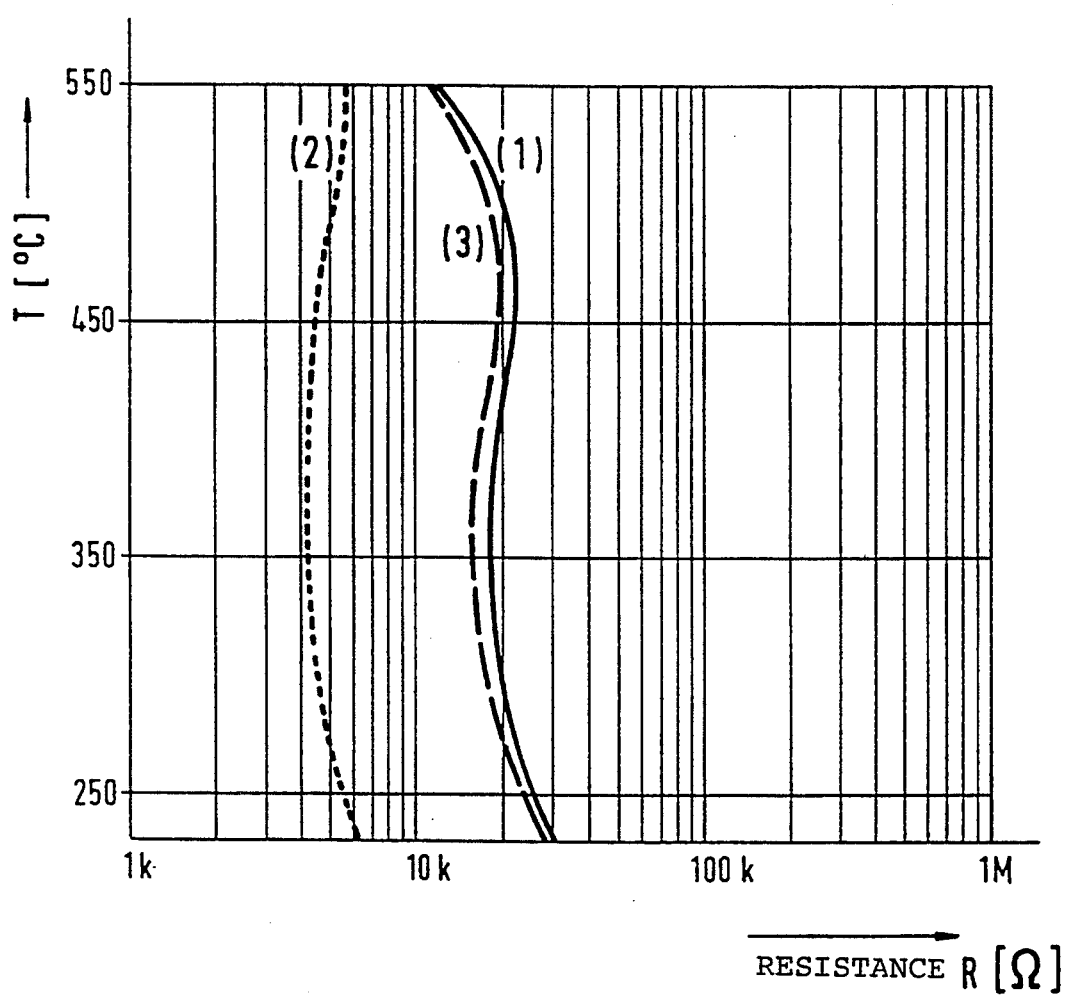
FIG. 3 is a graphic representation depicting resistance - temperature characteristics of yet another carbon monoxide sensor of the present invention as a logarithmic plot.

The drawing indicates the advantageous properties of the sensors according to the invention. FIGS. 1 to 3 show the resistance-temperature characteristics of various sensors as a logarithmic plot. Of these, FIG. 1 relates to a prior art sensor, FIG. 2 shows the properties of a sensor containing a n-type metal oxide which is doped with two dopants, one having an oxide of another metal with a maximum valency <4 and the other, an oxide of a metal which catalyses the reaction of carbon monoxide to carbon dioxide and FIG. 3 those of a sensor containing a n-type metal oxide which is doped with similar dopants and additionally contains an oxide of a metal of the fifth subgroup of the Periodic Table of the Elements. The doped n-type metal oxides have the following compositions:

FIG. 1: tin(IV) oxide with 4 mol % of magnesium oxide, 2 mol% of aluminum oxide, 3 mol % of copper(II) oxide FIG. 2: tin(IV) oxide with 0.10 mol % of magnesium oxide, 0.14 mol % of palladium oxide FIG. 3: tin(IV) oxide with 0.10 mol % of magnesium oxide, 0.10 mol % of palladium oxide, 0.005 mol % of tantalum(V) oxide All the figures show 3 curves which were measured in the sequence indicated by the numbers, namely, the first curve with a gas mixture of 5% by volume of oxygen, remainder nitrogen, and the second curve with a gas mixture of 5% by volume of oxygen, 1000 ppm of carbon monoxide, remainder nitrogen.

The third curve shows measurements with the gas mixture of the first curve.

It can be seen that the sensors according to the invention do not exhibit significant hysteresis, but that they do have a high sensitivity for carbon monoxide and, in particular, a considerably reduced dependence of the resistance or the conductivity on temperature, compared to the prior art. This applies particularly to the sensor according to FIG. 3.

We claim:

1. A sensor for the determination of carbon monoxide in a gas mixture comprising a doped n-type metal oxide whose electric conductivity is a function of the composition of the gas mixture, dopants for said metal oxide comprising (a) from 0.01 to 0.2 mol % of an oxide of another metal having a maximum valency <4 together with (b) from 0.01 to 0.2 mol % of an oxide of a metal, which catalyses the reaction of carbon monoxide to carbon dioxide and (c) from 0.001 to 0.1 mol % of an oxide of a metal of the 5th subgroup of the Periodic Table of the Elements.

2. The sensor according to claim 1, wherein the n-type metal oxide is tin(IV) oxide which is doped with magnesium oxide, palladium oxide and the oxide of a metal of the 5th subgroup of the Periodic Table of the Elements.

3. The sensor according to claim 1, wherein the oxide of a metal of the 5th subgroup of the Periodic Table of the Elements is tantalum (V).

4. The sensor according to claim 2, wherein the oxide of a metal of the 5th subgroup of the Periodic Table of the Elements is tantalum (V).

5. A sensor as defined in claim 1 for determining carbon monoxide in a gas mixture containing oxygen.

* * * * *